United States Patent
Lumpkin et al.

(10) Patent No.: US 7,540,855 B2
(45) Date of Patent: Jun. 2, 2009

(54) DISPOSABLE ASPIRATOR CASSETTE

(75) Inventors: Christopher F. Lumpkin, Steamboat Springs, CO (US); Shawn P. Mullen, Glenmoore, PA (US); John E. Richmond, Doylestown, PA (US)

(73) Assignee: Peregrine Surgical, Ltd., New Britain, PA (US)

( * ) Notice: Subject to any disclaimer, the term of this patent is extended or adjusted under 35 U.S.C. 154(b) by 37 days.

(21) Appl. No.: 11/809,505

(22) Filed: Jun. 1, 2007

(65) Prior Publication Data

US 2008/0300533 A1    Dec. 4, 2008

(51) Int. Cl.
*A61M 37/00* (2006.01)
*A61M 1/00* (2006.01)

(52) U.S. Cl. .................. 604/131; 604/152; 604/153; 604/319

(58) Field of Classification Search ............... 604/34, 604/131, 317–324, 326
See application file for complete search history.

(56) References Cited

U.S. PATENT DOCUMENTS

| | | | | |
|---|---|---|---|---|
| 3,866,608 A | * | 2/1975 | Reynolds et al. | 604/319 |
| 4,058,123 A | * | 11/1977 | May | 604/30 |
| 4,359,051 A | * | 11/1982 | Oczkowski | 604/344 |
| 4,475,904 A | * | 10/1984 | Wang | 604/119 |
| 4,522,623 A | * | 6/1985 | Lauterjung | 604/319 |
| 4,627,833 A | | 12/1986 | Cook | 604/34 |
| 4,735,610 A | | 4/1988 | Akkas et al. | 604/119 |
| 4,758,238 A | | 7/1988 | Sundblom et al. | 604/319 |
| 4,773,897 A | * | 9/1988 | Scheller et al. | 604/34 |
| 4,913,698 A | * | 4/1990 | Ito et al. | 604/22 |
| 4,963,131 A | | 10/1990 | Wortrich | 604/34 |
| 5,078,677 A | * | 1/1992 | Gentelia et al. | 604/6.15 |
| 5,163,900 A | | 11/1992 | Wortrich | 604/30 |
| 5,242,404 A | | 9/1993 | Conley et al. | 604/119 |
| 5,282,787 A | | 2/1994 | Wortrich | 604/30 |
| 5,302,093 A | | 4/1994 | Owens et al. | 417/474 |
| 5,342,313 A | | 8/1994 | Campbell et al. | 604/153 |
| 5,499,969 A | | 3/1996 | Beuchat et al. | 604/30 |
| 5,518,378 A | | 5/1996 | Neftel et al. | 417/477.2 |
| 5,542,918 A | | 8/1996 | Atkinson | 604/27 |
| 5,588,815 A | | 12/1996 | Zaleski, II | 417/477.2 |
| 5,676,530 A | | 10/1997 | Nazarifar | 417/360 |

(Continued)

FOREIGN PATENT DOCUMENTS

EP    0893603 B1    10/2002

*Primary Examiner*—Kevin C Sirmons
*Assistant Examiner*—William Carpenter
(74) *Attorney, Agent, or Firm*—Watov & Kipnes, P.C.; Kenneth Watov (57) ABSTRACT

An aspirator cassette includes a housing having first and second ends sealed off by first and second end caps, respectively. A partition mechanism is enclosed within the housing for dividing its internal volume into first and second regions. First and second fluid flow ports are mounted on the first and second end caps, respectively, to provide fluid flow paths into and from the first and second regions, respectively. When the first region is filled with liquid, its associated first port is connected to a vacuum source for sucking the liquid out of the region, whereby as the liquid is removed, the partition mechanism responds by decreasing the volume of the first region, and increasing the volume of the second region causing its second port to draw a vacuum for sucking fluid from an aspiration device connected to the second port.

39 Claims, 7 Drawing Sheets

U.S. PATENT DOCUMENTS

| | | | |
|---|---|---|---|
| 5,676,650 A | 10/1997 | Grieshaber et al. | 604/28 |
| 5,718,568 A | 2/1998 | Neftel et al. | 417/476 |
| 5,741,125 A | 4/1998 | Neftel et al. | 417/477.7 |
| 5,782,611 A | 7/1998 | Neftel et al. | 417/234 |
| 5,788,671 A * | 8/1998 | Johnson | 604/131 |
| 5,800,396 A * | 9/1998 | Fanney et al. | 604/151 |
| 5,810,766 A | 9/1998 | Barnitz et al. | 604/34 |
| 5,876,387 A * | 3/1999 | Killian et al. | 604/319 |
| 5,899,674 A | 5/1999 | Jung et al. | 417/477.2 |
| 6,059,544 A | 5/2000 | Jung et al. | 417/477.2 |
| 6,561,999 B1 | 5/2003 | Nazarifar et al. | 604/30 |
| 6,635,028 B1 * | 10/2003 | Ielpo et al. | 604/27 |
| 6,780,166 B2 | 8/2004 | Kanda et al. | 604/30 |
| 6,824,525 B2 | 11/2004 | Nazarifar et al. | 604/30 |
| 6,899,694 B2 | 5/2005 | Kadziauskas et al. | 604/35 |
| 6,921,385 B2 | 7/2005 | Clements et al. | 604/141 |
| 6,948,918 B2 | 9/2005 | Hansen | 417/395 |
| 7,001,356 B2 | 2/2006 | Kadziauskas et al. | 604/35 |
| 7,160,268 B2 | 1/2007 | Darnell et al. | 604/141 |
| 2004/0115068 A1 | 6/2004 | Hansen et al. | 417/379 |
| 2005/0131361 A1* | 6/2005 | Miskie | 604/350 |

* cited by examiner

DISPOSABLE ASPIRATOR CASSETTE

FIELD OF THE INVENTION

The present invention is related broadly to aspirating systems, and more particularly to such systems including disposable cassettes for receiving aspirated fluid from a site being irrigated, such as but not limited to a surgical site.

BACKGROUND OF THE INVENTION

Many surgical systems require instruments and devices that provide for the use of fluids to irrigate surgical sites, and further provide for the aspiration of the fluids from the surgical sites, typically on a continuous or selectively intermittent process during the surgery. In many such prior systems, surgical cassettes are used to collect fluid aspirated from the surgical sites, whereby after use, due to contamination from the fluids, the now contaminated cassettes are typically disposed of. Many of the known cassettes are very expensive, and represent increased surgical costs for hospitals, and other health providers that must use such cassettes. There has been a long felt need in the art to provide devices or mechanisms for preventing the contamination of expensive surgical cassettes, thereby permitting continuous use of the primary cassette during multiple surgeries, to offer substantial cost savings to the health providers.

A vitrectomy is an example common surgical procedure performed for retinal eye disorders that typically requires use of the aforesaid surgical systems. More specifically, a vitrectomy is performed to remove vitreous humor (jelly-like liquid) from the posterior segment or back of eye. To maintain the integrity of the eye while vitreous is being aspirated, balance salt solution is continually infused.

To perform a vitrectomy, the retinal surgeon uses one type of the aforesaid surgical systems known as a vitrectomy "unit." The vitrectomy unit serves as a "source pump" or "vacuum pump". Disposable components and instruments such as a Vitreous Cutter (cutter), Tubing Sets (tubing) and Cassette Reservoir (cassette) are attached to the vitrectomy unit. Together, the vitrectomy unit and disposable components make up a vitrectomy "system."

The vitrectomy unit itself is usually a large stand alone device that is not sterile, and is activated by the surgeon using a foot pedal. The disposable vitreous cutter is physically held by the surgeon and placed into the eye. When the vitrectomy unit is activated, vitreous is aspirated through the cutter and tubing.

The cassette is not handled by the surgeon during the operation. Rather, a circulating nurse secures the cassette to the vitrectomy unit. The cassette has three primary functions. First, relative to one example in the prior art, because of its special proprietary design, it allows the vitrectomy unit to activate.

Once the vitrectomy unit is activated by inserting the proprietary cassette, the surgeon is then permitted to control vacuum and/or aspiration flow rate via use of a foot pedal. Fluids may now be vacuumed and or/aspirated out of the eye via the cutter and carried away through the tubing for deposit into the cassette.

In most vitrectomy units, a cassette is required for activation. The cassette is generally produced as a disposable component. Prior to the start of each vitrectomy, a new cassette is opened and installed in the vitrectomy unit. A new cassette is used because in each case the cassette is contaminated from eye fluids. After the vitrectomy, the cassette is then thrown away per hospital protocol regarding bio-contamination.

In addition to being a reservoir for eye fluids, the cassette has another purpose. The cassette is specially designed with proprietary features to ONLY activate a proprietary vitrectomy unit for which it was designed. Therefore, use of a certain vitrectomy unit is dependent upon using the same company's proprietary cassette. This is how companies generate residual sales after selling a one time purchase of the vitrectomy unit.

Figure 1:
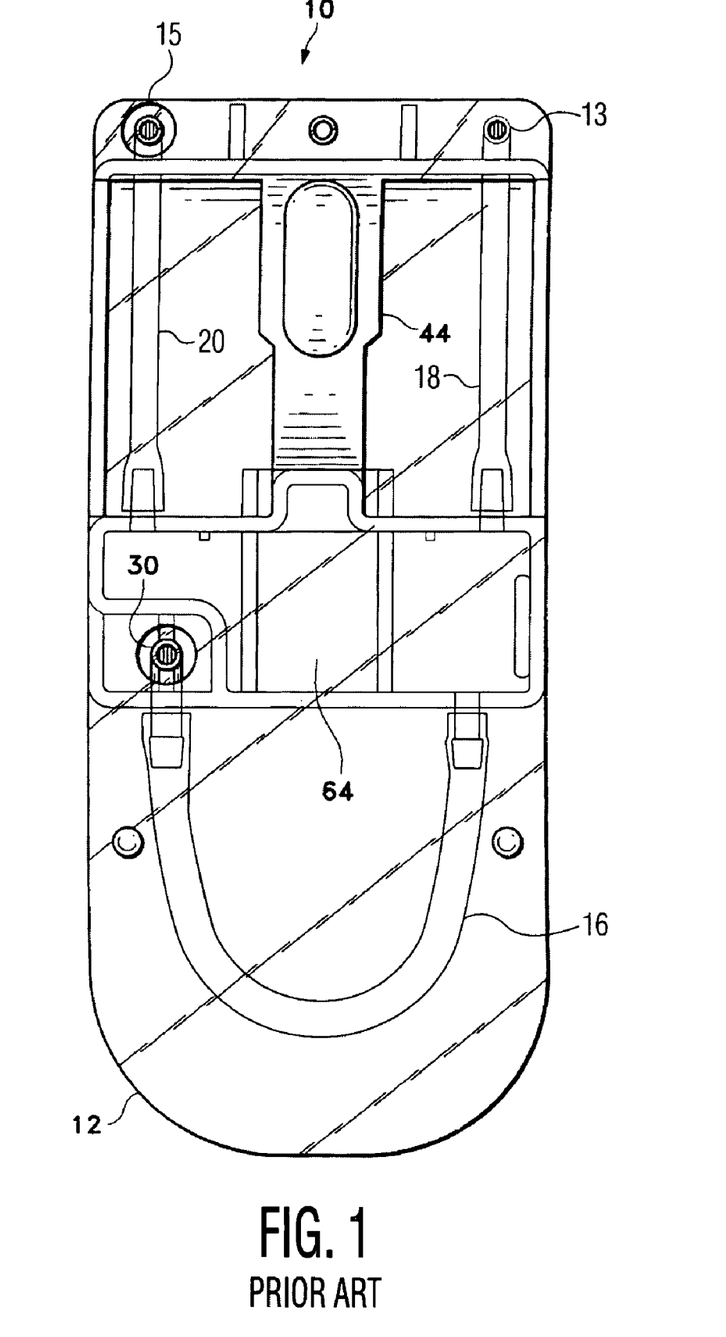
FIG. 1 is a front elevational view of a cassette in the prior art.
Figure 2:
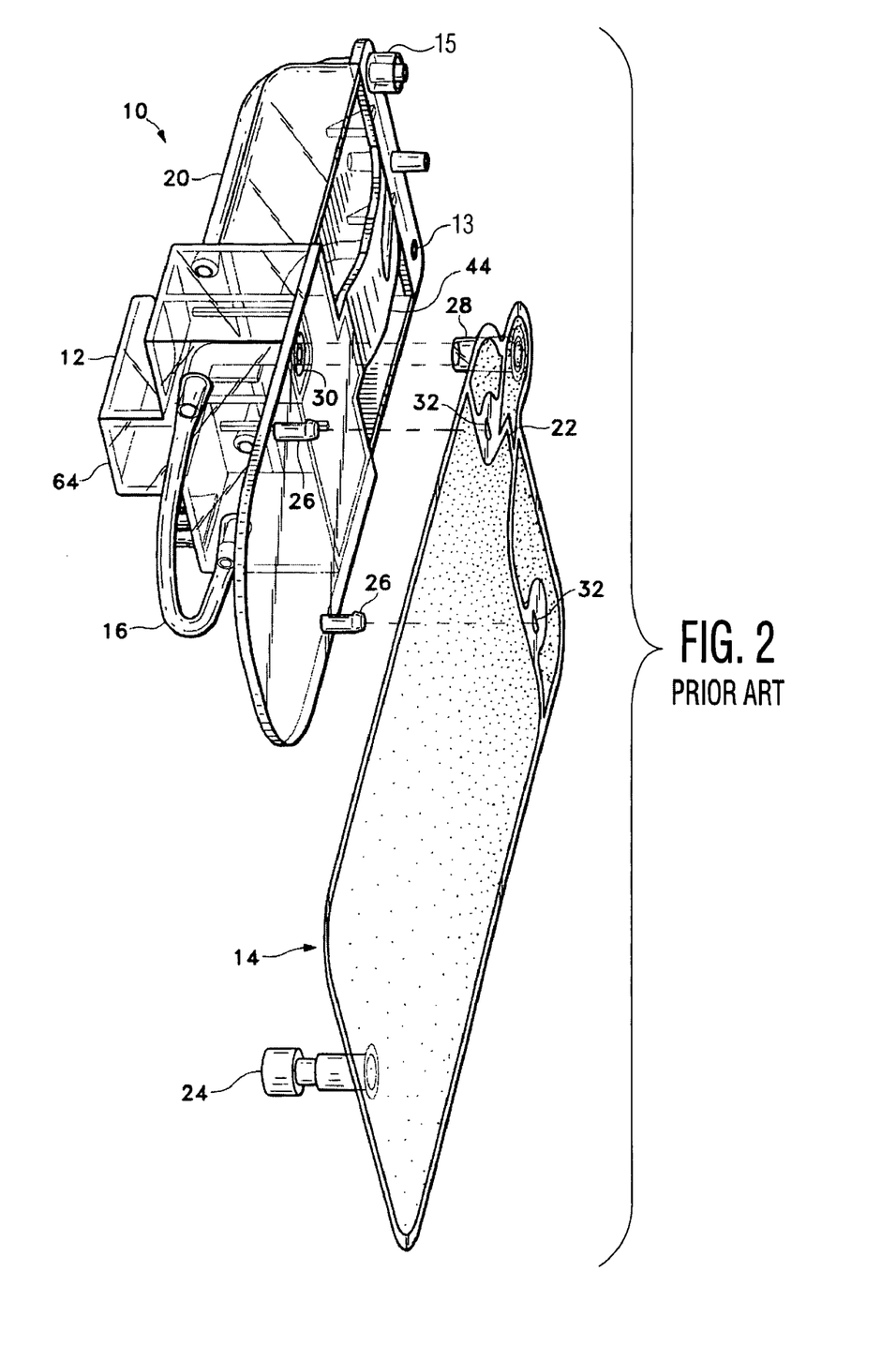
FIG. 2 is an exploded perspective or pictorial of the cassette of FIG. 1 in association with a drain bag.

An example of one such prior surgical cassette of a vitrectomy system is disclosed in Jung et al. U.S. Pat. No. 6,059,544, entitled "Identification System For A Surgical Cassette," issued on May 9, 2000. As shown in FIGS. 1 and 2 hereof, the cassette 10 includes a single piece plastic housing 12 that has a handle 44 for installing and removing the cassette 10 from a vitrectomy unit (not shown). The cassette 10 is a relatively complicated device, as described in the aforesaid patent. Certain, but not all of the features of cassette 10 will now be described. With further reference to FIGS. 1 and 2, cassette 10 further includes aspiration lines 18 and 20, a peristaltic pump tube 16 having one end connected to an output port 30. A drain bag 14 is provided, and includes holes 32 to allow it to hang from hooks 26 provided on the cassette 10. A port 28 of the drain bag 14 is secured to an output port 30 associated with peristaltic pump tube 16. The drain bag 14 further includes a one-way valve 22 for preventing the backup of fluid into the cassette 10, and a sampling port 24 for permitting a sample of fluid to be drawn from the bag for testing, or other purposes. The cassette 10 further includes a first vacuum input port 13, and a second vacuum port 15, as shown. Note both the cassette 10, and its associated drain bag 14, are provided by Alcon Laboratories, Inc., of Fort Worth, Tex. Due to the obvious complexity of the cassette 10, it represents a relatively high cost component for users, that must be disposed of after a first use, along with the associated drain bag or bags 13. Note that chamber 64 provides for receiving materials or aspirated liquid (contaminated eye fluid) drawn into chamber 64 through aspiration lines 18 and 20.

The present inventors recognized that if a method and device is developed for permitting users of the aforesaid cassette 10, and similar such cassettes, to continually use the cassettes, considerable cost savings will be provided. Accordingly, as described in detail below, the present inventors developed a disposable surgical cassette that is substantially inexpensive relative to the cost of surgical cassettes such as cassette 10, whereby the present inventive surgical cassette is disposable, while permitting extended continuous use of the cassette 10 when used in association therewith. However, the present invention is not limited to permitting continual use of the aforesaid Alcon cassette 10, and can be used in other aspirating systems. For example, it is expected that the present inventive cassette will also have use in surgical aspirating systems in both posterior and anterior surgical fields. In addition, it is expected that the present inventive cassette will have use in industrial systems.

SUMMARY OF THE INVENTION

The inventors have developed a unique secondary cassette having one application for vitrectomy surgeries that can adapt to any vitrectomy unit. This cassette is used in addition to a "proprietary primary cassette" already installed on the vitrectomy unit. During a vitrectomy, the new secondary cassette protects the primary cassette from contamination, and therefore the latter can be continually used in successive surgical procedures. Additionally, the integrity of the primary cassette is maintained and not compromised because it does not have to be removed after each surgery from the vitrectomy unit it was designed for.

The present secondary cassette has several functions. First, it acts as a reservoir for eye fluids so as not to allow contamination of known primary cassettes. Second, it works in tandem with existing primary cassettes to maintain a vacuum system for removing of vitreous and fluids. Third, it provides sterile or non-contaminated water to the primary cassette to keep it operational. Fourth, it serves as a barrier between contaminated fluids and sterile or non-contaminated water sent to the primary cassette.

In one embodiment of the invention, the present secondary cassette is set up and operates in the following manner. Specially designed tubing is attached to two separate luer ports located on opposing ends of the secondary cassette. Tubing from one luer port is attached to a vitreous cutter hand piece and extrusion instrument. Tubing from the other port is attached to the primary cassette. Inside the secondary cassette and sealed to the inside luer port (that goes to the vitreous cutter) is a pouch or bladder type receptacle. This pouch is for collection of fluids aspirated from the eye. The pouch can be provided by a thin walled collapsible bag consisting of a suitable material such as plastic or latex.

During set up, sterile water is poured into the present secondary cassette through a separate large opening (third port). This third port is designed to include a screw-on cap for sealing the port. The entire device is filled with sterile or non-contaminated water. During use, this water is suctioned out of the device through the non-pouch luer port and into the primary cassette. The water is necessary to circulate through the primary cassette during activation.

Using a foot pedal, a surgeon activates the vitrectomy unit to generate suction as needed. Suction is created when the vitrectomy unit aspirates sterile or non-contaminated water from the secondary cassette. When this occurs and water is suctioned out of the secondary cassette, the pouch inside the device expands and creates a reciprocating suction effect. When this occurs, intraocular fluids are aspirated into the cutter tip, up through tubing and into the pouch of the secondary cassette. Hence, fluids are suctioned out of the eye. When the procedure is completed, the contaminated secondary cassette, associated tubing and cutter are disposed. The primary cassette can be drained of the sterile water and left installed for the next procedure.

In another embodiment of the invention, the secondary cassette includes a sealed container of any desirable cross section, in which a collapsible bag is filled with sterile or non-contaminated fluid. The container is sealed in a manner making the container air tight. The open end of the collapsible bag is sealed around the inside portion of an output port located at one side of the cassette. The other chamber of the cassette is provided with an input port. In use, the output port is connected to a vacuum source for aspirating the sterile fluid out of the collapsible bag, whereby as the fluid is removed from the bag, the bag collapses and produces a vacuum in the interior portion of the cassette surrounding the bag. The input portal is connected to an operating device, such as but not limited to a surgical instrument, whereby the vacuum created in the interior space of the cassette surrounding the collapsible bag causes the irrigation fluid to be drawn from the aspirating device into the cassette for collection.

In yet another embodiment of the invention, for surgical applications, the input and output ports of either of the immediately above-described two embodiments each include mechanical fastening mechanisms for permitting attachment thereto.

In each of the above-described embodiments of the invention, for another and preferred embodiment, the secondary cassette includes a housing consisting of transparent material. Also the collapsible bag preferably consists of translucent or transparent material. As a result, a user can observe the extent of sterile or non-contaminating fluid left in the cassette at any time, and aspirating fluid drawn into the cassette or bag at any given time, dependent upon the method of use of the cassette. Note that in certain applications, the housing and/or bag can consist of opaque material. In yet another embodiment, the bag can be replaced by a piston.

BRIEF DESCRIPTION OF THE DRAWINGS

Various embodiments of the present invention will now be described with reference to the drawings, in which like items are identified by the same reference designation, wherein.

DETAILED DESCRIPTION OF THE INVENTION

Figure 3A:
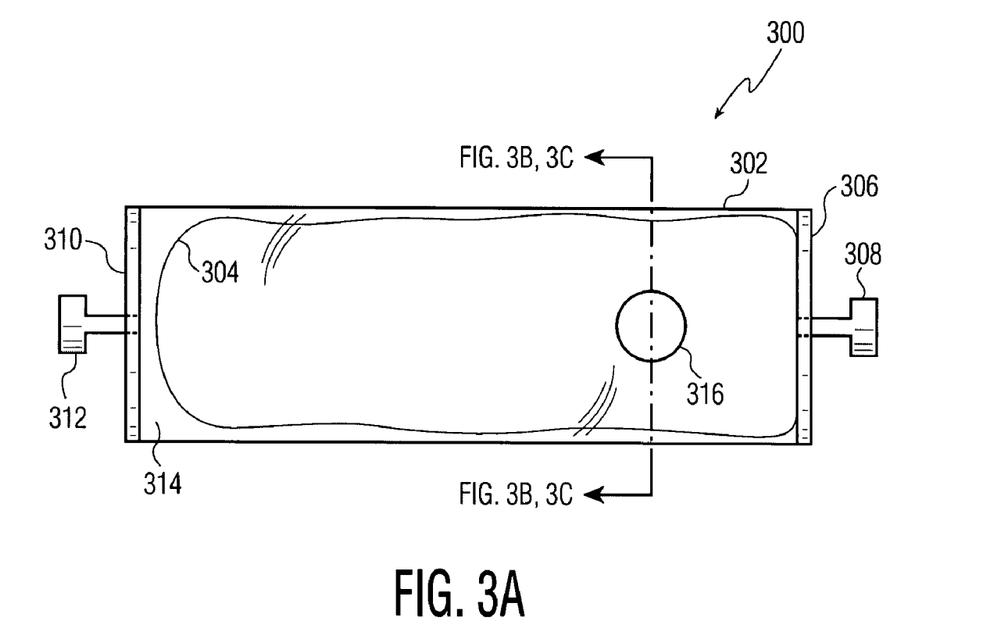
FIG. 3A is a front elevational view of a first embodiment of the invention.
Figure 3B:
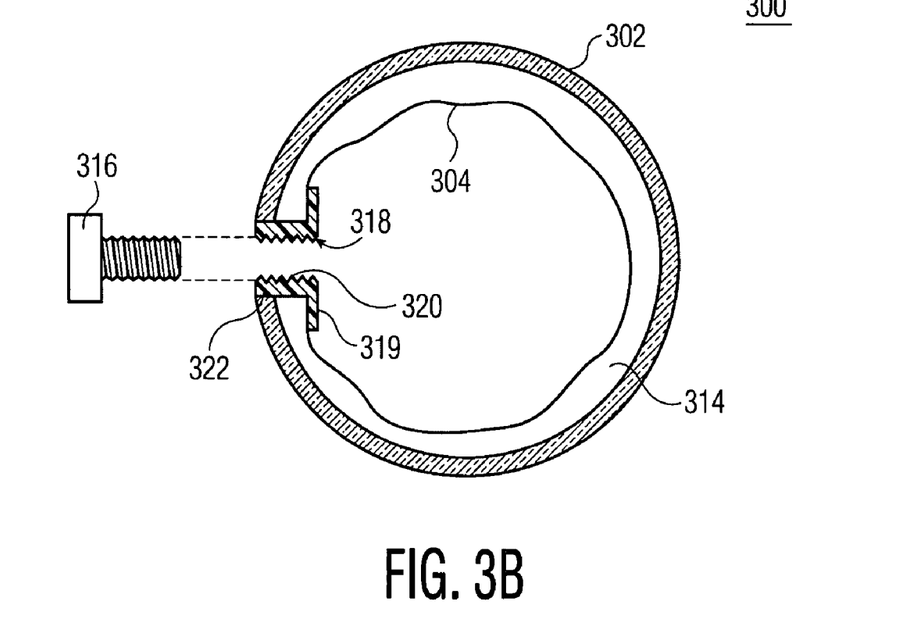
FIG. 3B is a cross-sectional view for one embodiment of the invention of FIG. 3A taken along 3B-3B thereof.
Figure 3C:
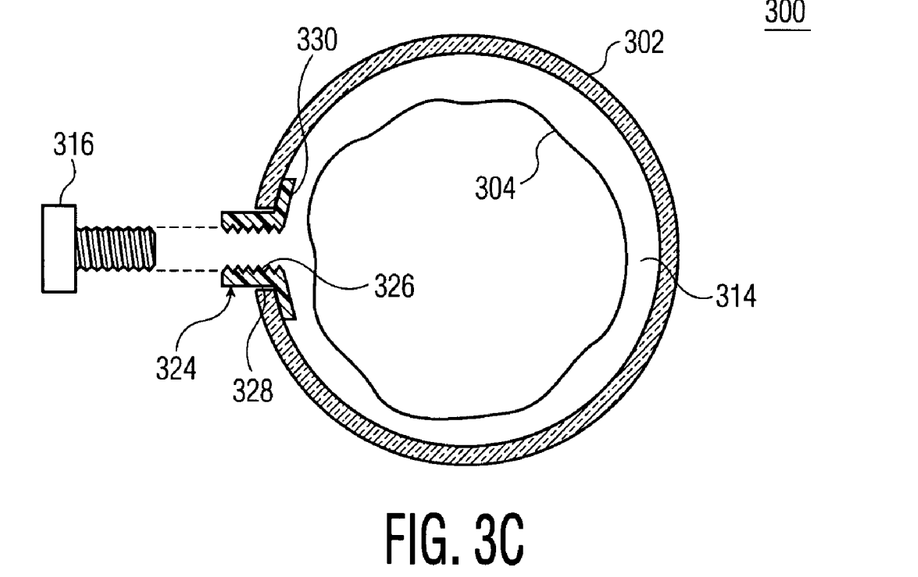
FIG. 3C is a cross-sectional diagram taken along 3C-3C for another embodiment of the invention relative to FIG. 3A.

In FIG. 3A, first and second embodiments of the present invention are shown. More specifically, in a first embodiment an aspirator cassette 300 includes in this example a cylindrical or tubular housing 302 enclosing a thin-walled flexible bag 304. One end of the housing 302 is sealed off by a first end cap 306 that includes a centrally located port 308 providing a fluid flow path therethrough into the interior of the bag 304. The other end of the housing 302 is sealed off by a second cap 310 that includes therethrough a second port 312 providing a fluid flow path into the interior space of volume 314 of housing 302 surrounding the bag 304. In this example, the cross section of the housing 302 is circular, but is not meant to be limiting in that the cross section can be made in any desirable shape, such as oval, elliptical, rectangular, and so forth. As will be described in greater detail below, a plug 316 is configured for in one embodiment of the invention (as shown in FIG. 3B) to provide access to the interior of the bag 304, and in another embodiment of invention (as shown in FIG. 3C) to provide access to the interior volume or space 314 of housing 302 surrounding the bag 304. Note that the plug 316 can be configured in many ways, such as being threaded for screw-in use, or for a frictional fit, or any other suitable configuration.

With further reference to FIG. 3B, a circular threaded collar 318 is provided with a circular flange 319 for sealing around the hole provided in the side of the bag 304. The flange 319 can be sealed to bag 304 through use of any suitable adhesive, such as silicone seal, for example. The collar 318 further includes an interior threaded short tubular member 320 having portions of its free end secured in an airtight connection to a hole 322 to the side of the housing 302, as shown. Again, the securement can be made through use of a suitable adhesive, or electronic welding, for example, to provide an airtight seal. In the embodiment of the invention of FIG. 3B, the plug 316 is removed from the housing 302 and bag 304 to permit access to the interior of the bag 304.

In the embodiment of the invention of FIG. 3C, a threaded collar 324 includes a short interior threaded tubular portion 326 secured in an airtight manner within a hole 328 in a side portion of the housing 302. To further insure a good mechanical and airtight connection, the collar 324 also includes a circular flange portion 330 that is secured around the interior wall portions of the housing 302, via use of any suitable adhesive, such as silicone seal, for example. In this embodiment, the plug 316 is unscrewed and removed from the collar 324 for permitting access to the interior volume 314 of the housing 302.

Figure 4:
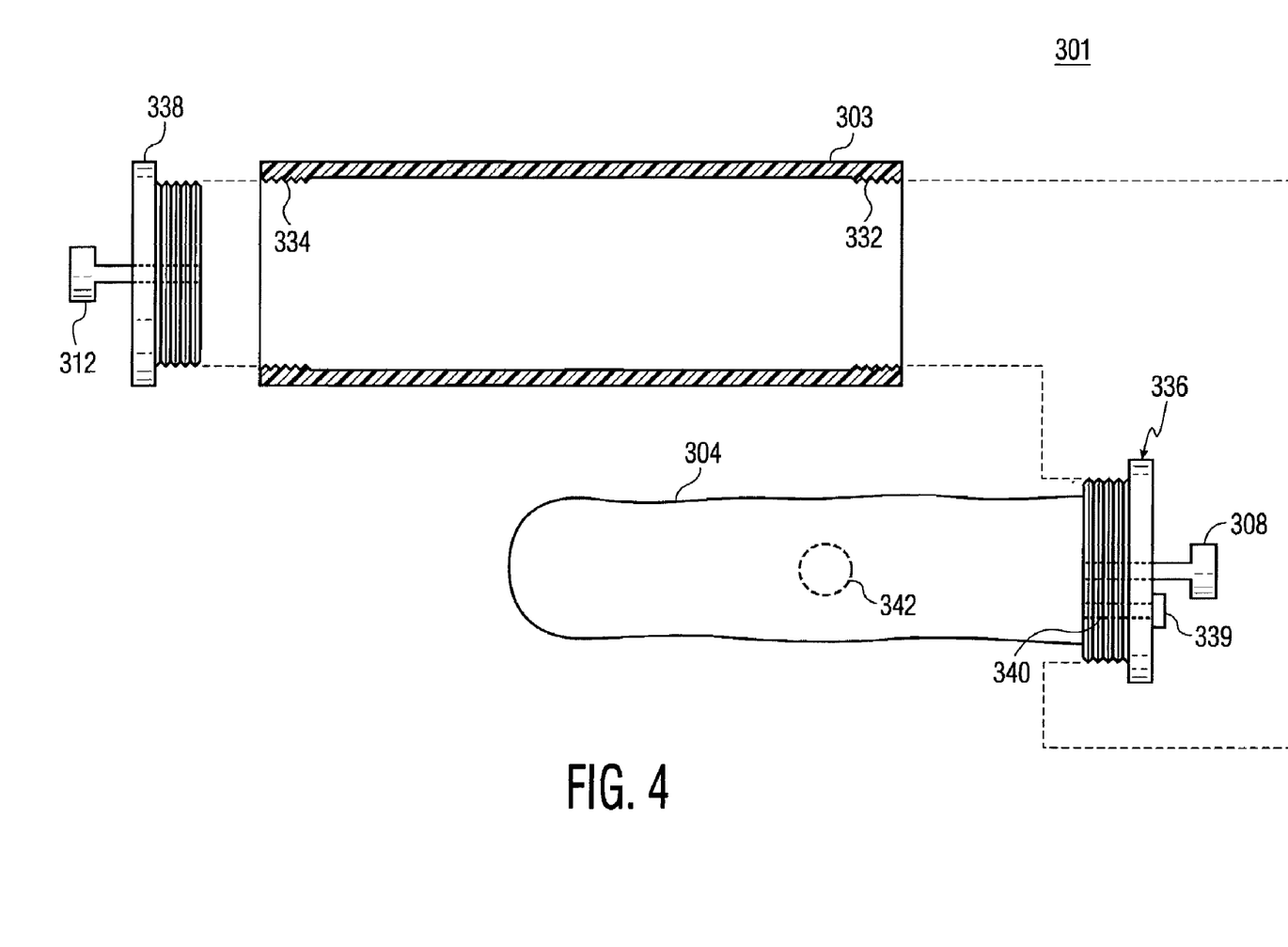
FIG. 4 is an exploded longitudinal cross-sectional and cut-away view of an exploded assembly diagram for another embodiment of the invention.

A third embodiment of the invention is shown in FIG. 4. In this embodiment, the housing 302 includes an interior threaded end portion 332 at one end, and a similar interior threaded portion 334 at its other end. A threaded end cap 336 is provided for screwing into and providing an airtight seal at the threaded end 332 of housing 302. Cap 336 includes a first port 308 providing a fluid path through the cap into the interior section of a thin-walled collapsible bag 304. The open end of the bag 304 is sealed in an appropriate airtight manner to the outer circumferential interior portion of the cap 336, as shown. A screw-in plug 339 is provided for securement into a threaded hole 340 through the cap 336, for permitting easy access to the interior of the bag 304. Alternatively, rather than using the removable plug 339, a sealable port 342 can be provided for providing access into the interior bag 304 through a circular sidewall opening 322 of housing 302, as shown in the embodiment of FIG. 3B. The threaded cap 338 is provided at the other end of the housing 302 for screwing into an interior end-threaded portion 334 thereof for providing an airtight seal. A second port 312 is provided through the cap 338, as shown.

Figure 5:
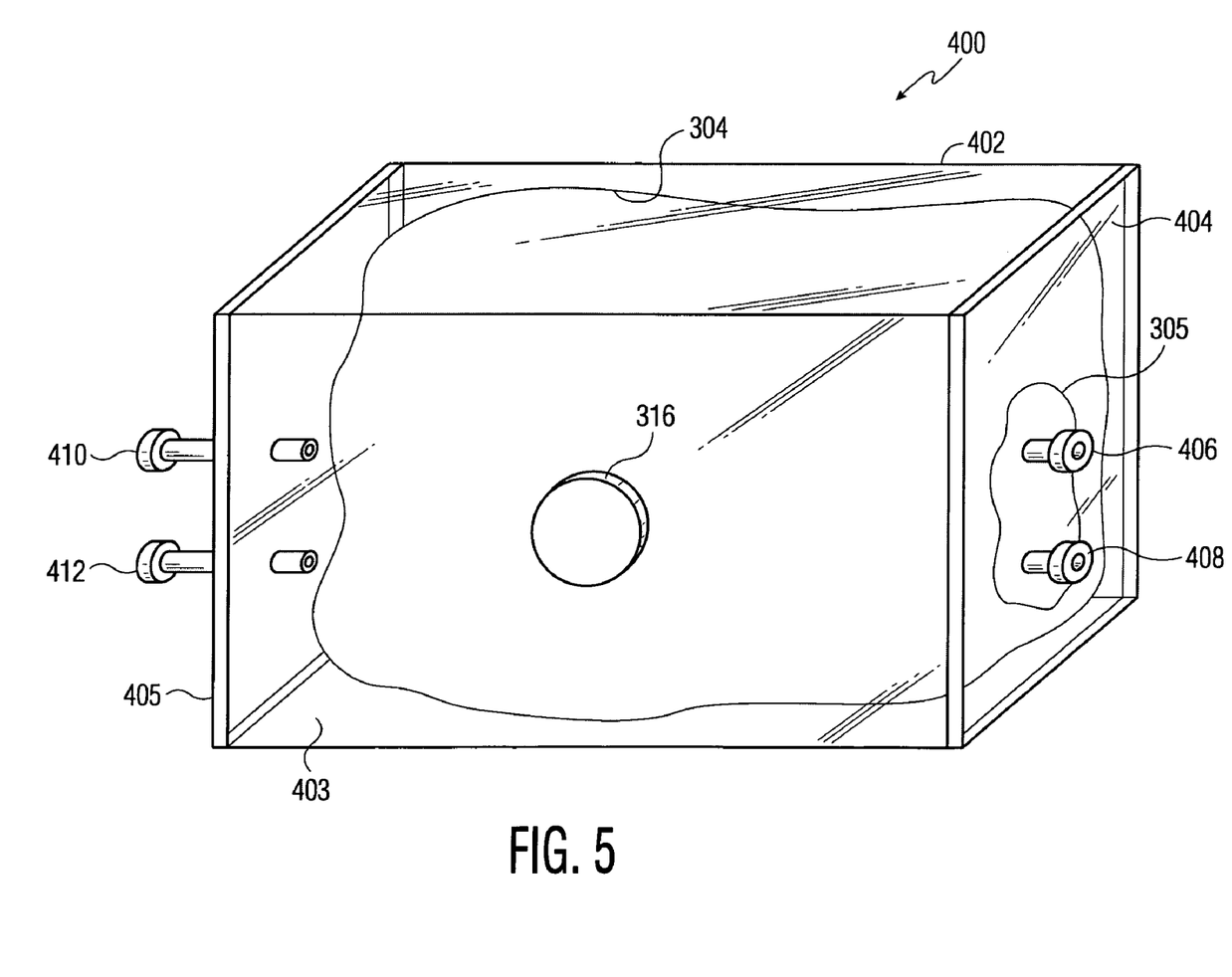
FIG. 5 is a pictorial view of yet another embodiment of the invention.

In a fourth embodiment of the invention, as shown in FIG. 5, a disposable cassette 400 is provided by housing 402 having a rectangular cross section. However, the shape of the housing 402 is not meant to be limiting as shown, and can be configured to have any desirable cross section, such as circular, oval, elliptical, and so forth. A cap 404 is provided at one end of the housing for providing an airtight seal at that end. Similarly, at the other end of the housing, a cap 406 is provided for insuring an airtight seal at that end. The housing 402 encloses a collapsible bag 304, as in other embodiments of the invention. A plug 316 is provided on one side of a housing 402 for either providing in one embodiment access to the interior of the bag 304 in a manner substantially similar to that shown in the embodiment of the invention of FIG. 3B, or for providing access to the interior portion of the housing 402 surrounding the bag 304 substantially as shown in the embodiment of the invention of FIG. 3C. First and second ports 406 and 408 are provided at the end cap 404 for access into the interior of bag 304, whereby the open end 305 of the bag 304 is sealed to the inside surface of the cap 404 in a manner surrounding the ports 406 and 408. A second pair of ports 410 and 412 are provided in the end cap 405 for access into the interior volume of the housing 402 surrounding the bag 304, as shown.

The materials used for the various embodiments of the invention will now be described for purposes of example only, and are not meant to be limiting, and that any other suitable material can be used. The housing 302 of FIG. 3A, 303 of FIG. 4, 402 of FIG. 5, and 502 of FIG. 6 (see below), preferably consist of any suitable transparent material such as Plexiglas, for example. The end caps 306 and 310 of FIG. 3A, 336 and 338 of FIG. 4, 404 and 405 of FIG. 5, and 510 and 508 of FIG. 6, can consist of any suitable material, such as Delrin®. The ports 308 and 312 of FIG. 3A, and of FIG. 4, and the ports 406, 408, 410, 412 of FIG. 5, can be provided by Luer-Lok®s for surgical applications, and otherwise can be provided by flow ports, or other mechanical fastening mechanisms, depending upon the application. The plug 316 of FIGS. 3A, 3B, 3C and FIG. 5, and the plug 339 of FIG. 4, can each consist of Delrin®, or any other suitable material. As previously mentioned, the thin-wall collapsible pouch or bag 304 can be provided by any suitable material, such as polyurethane, latex, and so forth.

Operation of the various embodiments of the invention will now be described. In a first embodiment of the invention as shown in FIGS. 3A and 3B, the plug 316 is removed from the housing 302, to permit liquid to be put into and substantially fill the bag 304. In surgical applications, the liquid can be saline, or any other suitable non-contaminating fluid, for example. In certain applications, the liquid may be required to be sterile. After filling the bag 304 with liquid, the plug 316 is reinstalled in order to seal off the bag 304. Thereafter, the port 308 is connected to a vacuum source for drawing liquid from the bag 304 at a desired flow rate, and the port 312 is connected to a device for aspirating fluid from a surgical site, for example, or some other site that is being irrigated. As fluid or liquid is sucked out of the bag 304, it collapses creating a vacuum within the interior space 314 of the housing 302, this vacuum being provided at port 312 for drawing fluid from the aspirating device to the interior space 314 of housing 302. A further example of use of the present invention, as with this first embodiment and the other four embodiments of the invention, the first port of output port 308 can be a Luer-Lok®, connected by appropriate tubing to one of the vacuum input ports 13 or 15 of the Alcon cassette 10. Upon a vacuum being provided at the input port 13 or 15, via operation of the peristaltic pump creating a vacuum in tube 16, fluid from the bag 304 of the present cassette 300 is drawn through the input port 13 or 15 of the Alcon cassette 10, and ultimately from the Alcon cassette 10 into the drain bag 14. In this example, upon completion of the surgical procedure, the cassette 300 is removed from the Alcon cassette 10, and disposed of. The Alcon cassette 10 is drained of the saline fluid or other fluid collected, and the associated drain bag emptied, permitting reuse in multiple procedures of both the Alcon cassette 10, and the drain bag 14. The substantially less expensive cassette 300 is disposed of.

In a second embodiment of the invention as shown, FIGS. 3A and 3C, the ultimate operation of the invention is substantially similar to that of the first embodiment, except that the port 312 is connected to the vacuum source, such as input port 13 or 15 of the Alcon cassette 10, and the port 308 of the cassette 300 is connected to the aspirating device. Initially, the plug 316, as shown in FIG. 3C, is for permitting saline solution or sterile liquid to be put into the space 314 of the cassette 300 surrounding the bag 304. After the liquid is so installed, the plug 316 is screwed back into the threaded collar 304 for providing an airtight and fluid tight seal. When the vacuum source is applied to the port 312, the vacuum source begins to draw fluid or liquid from the interior space of volume 314 of cassette 300, causing the collapsible bag to expand, in turn creating a vacuum at the port 308 for drawing fluid from an aspirating device connected thereto into the bag 304. As bag 304 expands, it increases its interior volume, and causes a decrease in the volume within cassette 300 surrounding bag 304. When the surgical or industrial process is completed, as with the first embodiment of the invention, the cassette 300 is removed and disposed of. In certain applications, it may be required that when the bag 304 becomes filled with aspirating fluid, in the second embodiment of the invention, or when the interior volume 314, of the cassette 300 becomes filled with aspirated fluid, as with the first embodiment of the invention described above, that the particular surgical or industrial operation is temporarily stopped, in order to permit replacement of the a new cassette 300 for the spent cassette 300.

Operation of the third embodiment of the invention is shown in FIG. 4 is substantially similar to that of the aforesaid first two embodiments of the invention. More particularly, in one use of the third embodiment of the invention, the caps 336 and 338 are installed as shown with the bag 304 secured to the cap 336 as previously described. Next, the plug 339 is removed from the cap 336 to permit the bag 304 to be filled with saline solution or a sterile solution such as sterile water, dependant upon the application. The ports 308 and 312 are connected as previously described for the embodiment of the invention of FIG. 3B, and operation of the third embodiment is then the same as that of the first embodiment of the invention. The alternative cassette 301 is then disposed of after use. Contrariwise, the third embodiment of the invention can be operated as previously described for the second embodiment of the invention of FIGS. 3A and 3C. Specifically, the cap 336 along with the bag 304 secured thereto is screwed into the threaded end 332 of the housing 303. The cap 338 is removed, and saline solution or a sterilized liquid such as sterilized water is fed into the volume of the housing 303 surrounding the bag 304. Thereafter, the cap 338 is secured to the threaded end portion 334 of the housing 303. The port 312 is then connected to a vacuum source for drawing fluid from the interior volume of housing 303, thereby causing the bag 304 to again expand, for creating a vacuum at the port 308, the latter being connected to an aspirating device drawing fluid into the bag 304, as described for the second embodiment of the invention.

Operation of the fourth embodiment of the invention as shown in FIG. 5 will now be described. In one mode of operation, the plug 316 is removed for filling the bag 304 with saline solution or an appropriate sterilized liquid, for example, the plug 316 will then be reinstalled into the housing 402 and bag 304. Next, the ports 406 and/or 408 are connected to a vacuum source for drawing liquid from the bag 304, and the ports 410 and/or 412 are connected to an aspirating device, for drawing fluid or liquid therefrom into the interior volume 403 of the housing 402 surrounding the bag 304, in a manner similar to that described for embodiments of the invention described above. Alternatively, in the alternative configuration described for the embodiment of the invention of FIG. 3C, the plug 316 is removed for providing access to the interior volume 403 of the housing 402 surrounding the bag 304, and the interior volume 403 is filled with an appropriate saline solution, or sterilized fluid, or other appropriate liquid, as required, and the plug 316 is then reinstalled. Thereafter, either one or both of the ports 410, 412 are connected to a vacuum source for drawing fluid from the interior space of the housing 402, causing the bag 304 to expand, in turn creating a vacuum in ports 406 and 408. The ports 406 and/or 408 are connected to aspirating devices for drawing liquid therefrom into the bag 304, in a manner similar to that described above for previous embodiments of the invention.

Figure 6:
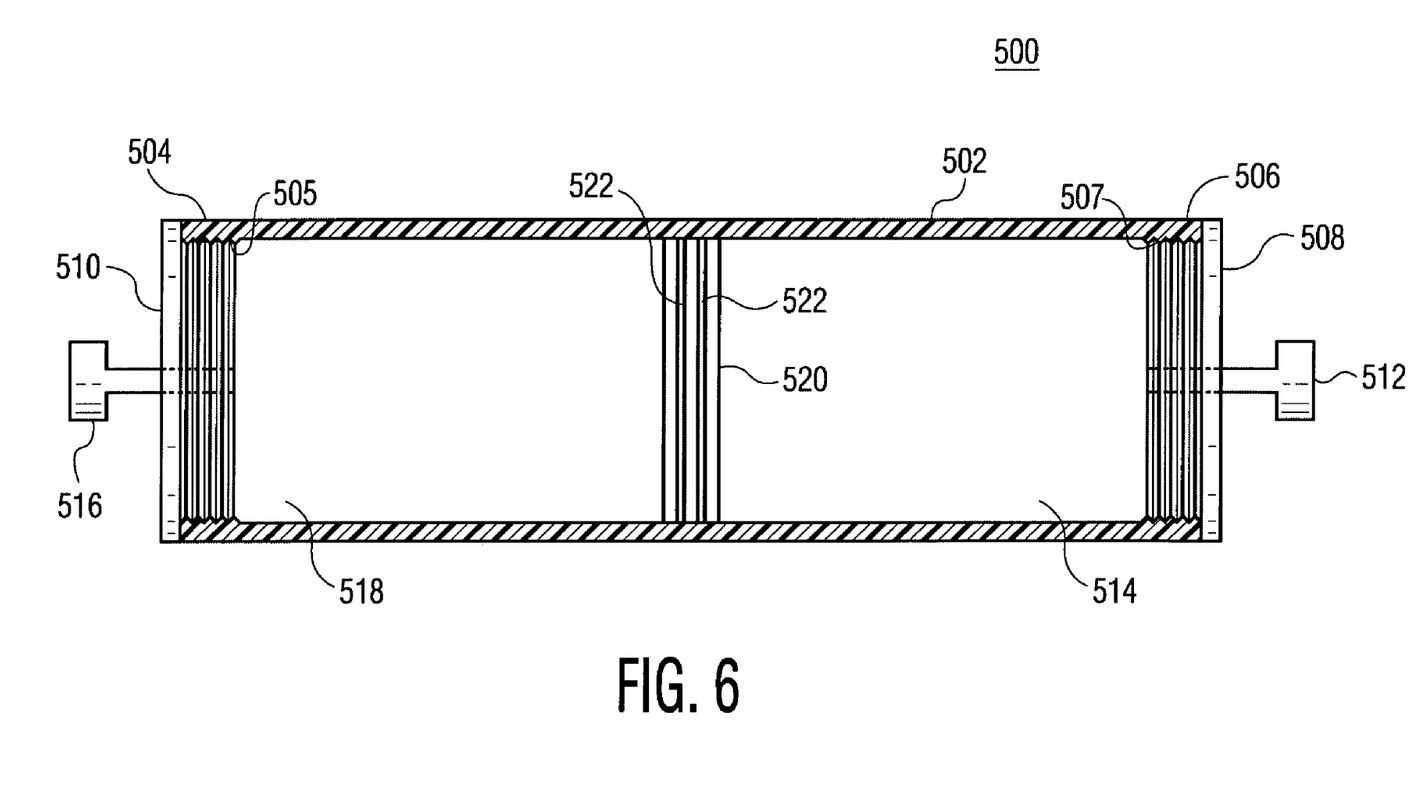
FIG. 6 is a front elevational view of a cassette for another embodiment of the invention.

With reference to FIG. 6, a fifth embodiment of the invention is shown. In this embodiment, a cassette 500 includes a housing 502, having female threads 505 provided at each of a first end 504, and female threads 507 provided at a second end 506. A male threaded end cap 508 is screwed into the end 506 for sealing off that end, as is a male threaded second end cap 510 screwed into the other end 504 for sealing off that end. A fluid port 512 is mounted on the end cap 508 for providing a fluid flow path into a first volume region 514 of housing 502. Similarly, another fluid flow port 516 is mounted on the end cap 510 for providing a fluid flow path into a second volume region 518 of the housing 502. A piston 520 is slideably mounted within the housing 502, and depending upon its position therein, determines the volume of the first region 514, and the volume of the second region 518. In this example, the piston 520 is provided with two O-rings 522 secured within grooves (not shown) around the circumference of the piston 520. Note that in one application, the ports 512 and 516 can be provided by Luer-Lok®s, respectively. As an example of the operation of this embodiment of the invention, assume that port 516 is configured for connection to a vacuum source, whereas port 512 is configured for connection to the output port of an aspirator device. Assume further that the piston 520 is located proximate the end cap 508, maximizing the volume of the second region 518, which is initially filled with a liquid, such as saline, for example, but not limited thereto. When the vacuum source is connected to port 516, it begins to suck or draw liquid out of region 518, in turn causing the piston 520 to move toward the opposite end at 510. As piston 520 begins to move towards end cap 510, a vacuum is created in the region 514 of housing 502, whereby the vacuum is applied via port 512 to the aspirator device, causing fluid to be sucked therefrom into the volume of the region 514. This process continues until the piston 520 is proximate to the end cap 510, as a result of the liquid in region in 518 having been completely drawn away therefrom by the vacuum source. At this point, it is expected that the cassette 500 will be removed from the aspirator system, discarded, and replaced by a new cassette 500, if the aspirating operation or procedure is to be continued.

Although various embodiments of the invention are shown and described, they are not meant to be limiting. Those of skill in the art may recognize certain modifications to these embodiments, which modifications are meant to be covered by the spirit and scope of the appended claims. For example, the housing 302, 303, 402, and/or 502 can consist of metal, glass, a suitable plastic, or any other suitable material.

We claim:

1. An aspirating system, comprising:
   a surgical device including an aspirating output port;
   an aspirating unit including a vacuum port;
   a primary cassette having a vacuum input port for connection to the vacuum
   port of said aspirating unit, and a vacuum output port;
   a disposable secondary cassette including:
   a housing having first and second opposing open ends between which a hollow cavity or interior volume is provided;
   first and second caps secured to said first and second ends, respectively, for providing an air tight seal therewith;
   partition means installed within said housing for dividing the volume into first and second regions having an air tight and fluid seal therebetween, said first and second regions being located between interior sides of said first and second caps, respectively;
   first and second ports mounted onto and through said first and second caps, respectively, for providing a fluid pathway into or out of said first and second regions, respectively, said first region being filled with a fluid or liquid, and said second region with ambient air;
   said first port being connected to said vacuum output port of said primary cassette, and said second port being connected to said aspirating output port of said surgical device, whereby as said primary cassette vacuum port source sucks fluid out of said first region, said partition means responds by decreasing the volume of said first region, and increasing the volume of said second region, thereby 25 producing a vacuum at said second port for sucking fluid from said surgical device into said second region of said housing.

2. The aspirating system of claim 1, wherein said partition means of said secondary cassette includes:
a thin walled collapsible bag having an opening secured to and sealed in an air tight manner to the interior side of said first cap, with an interior portion of said first port extending into said opening of said bag, the interior of said bag providing said first region.

3. The aspirating system of claim 1, wherein said partition means of said secondary cassette includes:
a thin walled collapsible bag having an opening secured to and sealed in an air tight manner to an interior side of said second cap, with an interior portion of said second port extending into said opening of said bag, the interior of said bag providing said second region.

4. The aspirating system of claim 1, wherein said partition means of said secondary cassette includes:
a piston moveable between said first and second regions.

5. The aspirating system of claim 1, wherein the secondary cassette further includes a removable plug mechanism installed through a side wall of said housing into said first region, for permitting said 4 first region to be filled with fluid and sealed.

6. The aspirating system of claim 2, wherein the secondary cassette further includes means for providing access to the interior of said bag.

7. The aspirating system of claim 6, wherein said access means of the secondary cassette includes:
a mounting collar having an internally threaded shank portion terminating to a circular flange encircling a hole through said shank, circumferential portions of said bag surrounding a hole therein being secured to said circular flange, a free end portion of said shank portion being secured within a hole in a side of said housing; and
a plug configured for screwing into said mounting collar to seal off the hole in said bag, said plug being removable to permit access to the interior of said bag.

8. The aspirating system of claim 3, wherein the secondary cassette further includes means for providing access to the interior of said bag.

9. The aspirating system of claim 8, wherein said access means of the secondary cassette includes:
a mounting collar having an internally threaded shank portion terminating to a circular flange encircling a hole through said shank, circumferential portions of a side of said housing surrounding a hole therein being secured to said circular flange with said shank portion secured in said hole; and a plug configured for screwing into said mounting collar to seal off the hole in said housing, said plug being removable to permit access to the interior of said housing surrounding said bag.

10. The aspirating system of claim 1, wherein 2 said housing of said secondary cassette consists of transparent material.

11. The aspirating system of claim 1, wherein 2 said housing of said secondary cassette consists of opaque material.

12. The aspirating system of claim 1, wherein said housing of said secondary cassette consists of material selected from the group consisting of glass, a suitable plastic, and metal.

13. The aspirating system of claim 1, wherein said first and second caps of said secondary cassette consist of plastic material.

14. The aspirating system of claim 2, further including:
said first and second ends of said housing having female threads on inside portions thereof, respectively; and said first and second caps each having male threaded end portions for screwing onto said first and second ends of said housing, respectively.

15. The aspirating system of claim 14, wherein said first cap further includes:
a female threaded through hole providing a fluid passageway into said bag; and
a plug configured for screwing into the through hole of said cap to seal off the interior of said bag.

16. The aspirating system of claim 3, further including:
said first and second ends of said housing having female threads on inside portions thereof, respectively; and
said first and second caps each having male threaded end portions for screwing onto said first and second ends of said housing, respectively.

17. The aspirating system of claim 1, wherein said housing of said secondary cassette has a circular cross section.

18. The aspirating system of claim 1, wherein said housing has a rectangular cross section.

19. The aspirating system of claim 1, further including:
third and fourth ports mounted onto and through said first and second caps, respectively, for providing a fluid pathway into or out of said first and second regions, respectively.

20. The aspirating system of claim 1, wherein said partition means of the secondary cassette includes a piston providing an air tight seal between said first and second regions, said piston being freely slideable between the first and second ends of said housing.

21. The aspirating system of claim 20, further including:
said first and second ends of said housing having female threads on inside portions thereof, respectively; and
said first and second caps each having male threaded end portions for screwing onto said first and second ends of said housing, respectively.

22. A vitrectomy system comprising:
a vitrectomy unit;
a primary cassette including a vacuum port, and being configured for plugging into said vitrectomy unit to activate the same;
said vitrectomy unit being operable with said primary cassette to cause a vacuum to be produced at the vacuum port of the primary cassette;
a vitreous cutter including an aspirating port;
a disposable secondary cassette installed between the vacuum port of said primary cassette and the aspirating port of said vitreous cutter, to receive contaminated eye fluid in a manner isolating the primary cassette from any contact with the eye fluid, thereby avoiding contamination of the primary cassette and making it available for continuous use, said secondary cassette comprising:
a housing having first and second opposing open ends between which a hollow cavity or interior volume is provided;
first and second caps secured to said first and second ends, respectively, for providing an air tight seal therewith;
partition means installed within said housing for dividing the volume into first and second regions having an air tight and fluid seal therebetween, said first and second regions being located between interior sides of said first and second caps, respectively;

first and second ports mounted onto and through said first and second caps, respectively, for providing a fluid pathway into or out of said first and second regions, respectively, said first region being filled with a medically non-contaminating fluid or liquid, and said second region with ambient air; and said first port being connected to the vacuum port of said primary cassette, and said second port being connected to the aspirating port of said vitreous cutter, whereby a vacuum produced at said vacuum port of said primary cassette sucks non-contaminating fluid out of said first region of said housing, said partition means responds by decreasing the volume of said first region, and increasing the volume of said second region, thereby producing a vacuum at said second port for sucking eye fluid from said aspirating cutter into said second region of said housing.

23. The vitrectomy system of claim 22, wherein said partition means of said secondary cassette includes:
a thin walled collapsible bag having an opening secured to and sealed in an air tight manner to the interior side of said first cap, with an interior portion of said first port extending into said opening of said bag, the interior of said bag providing said first region.

24. The vitrectomy system of claim 22, wherein said partition means of said secondary cassette includes:
a thin walled collapsible bag having an opening secured to and sealed in an air tight manner to an interior side of said second cap, with an interior portion of said second port extending into said opening of said bag, the interior of said bag providing said second region.

25. The vitrectomy system of claim 22, wherein said partition means of said secondary cassette includes: a piston moveable between said first and second regions.

26. The vitrectomy system of claim 22, wherein said secondary cassette further includes a removable plug mechanism installed through a side wall of said housing into said first region, for permitting said first region to be filled with fluid and sealed.

27. The vitrectomy system of claim 23, wherein said secondary cassette further includes:
a mounting collar having an internally threaded shank portion terminating to a circular flange encircling a hole through said shank, circumferential portions of said bag surrounding a hole therein being secured to said circular flange, a free end portion of said shank portion being secured within a hole in a side of said housing; and
a plug configured for screwing into said mounting collar to seal off the hole in said bag, said plug being removable to permit access to the interior of said bag.

28. The vitrectomy system of claim 24, wherein the secondary cassette further includes:
a mounting collar having an internally threaded shank portion terminating to a circular flange encircling a hole through said shank, circumferential portions of a side of said housing surrounding a hole therein being secured to said circular flange with said shank portion secured in said hole; and
a plug configured for screwing into said mounting collar to seal off the hole in said housing, said plug being removable to permit access to the interior of said housing surrounding said bag.

29. The vitrectomy system of claim 22, wherein said housing of said secondary cassette consists of transparent material.

30. The vitrectomy system of claim 22, wherein said housing of said secondary cassette consists of material selected from the group consisting of glass, a suitable plastic, and metal.

31. The vitrectomy system of claim 22, wherein said first and second caps of said secondary cassette consist of plastic material.

32. The vitrectomy system of claim 23, further including:
said first and second ends of said housing having female threads on inside portions thereof, respectively; and
said first and second caps each having male threaded end portions for screwing onto said first and second ends of said housing, respectively.

33. The vitrectomy system of claim 32, wherein said first cap further includes:
a threaded through hole providing a fluid passageway into said bag; and
a plug configured for screwing into the threaded through hole of said cap to seal off the interior of said bag.

34. The vitrectomy system of claim 24, further including:
said first and second ends of said housing having female threads on inside portions thereof, respectively; and
said first and second caps each having male threaded end portions for screwing onto said first and second ends of said housing, respectively.

35. The vitrectomy system of claim 22, wherein said housing of said secondary cassette has a circular cross section.

36. The vitrectomy system of claim 22, wherein said housing of said secondary cassette has a rectangular cross section.

37. The vitrectomy system of claim 22, further including:
third and fourth ports mounted onto and through said first and second caps, respectively, for providing a fluid pathway into or out of said first and second regions, respectively.

38. The vitrectomy system of claim 22, wherein said partition means of said secondary cassette includes a piston providing an air tight seal between said first and second regions, said piston being freely slideable between the first and second ends of said housing.

39. The vitrectomy system of claim 38, further including:
said first and second ends of said housing having female threads on inside portions thereof, respectively; and
said first and second caps each having male threaded end portions for screwing onto said first and second ends of said housing, respectively.

* * * * *